United States Patent [19]

Imai et al.

[11] Patent Number: 4,665,238

[45] Date of Patent: * May 12, 1987

[54] PROCESS FOR THE SYNTHESIS OF ALKYLAROMATIC COMPOUNDS

[75] Inventors: Tamotsu Imai; Paul T. Barger, both of Mount Prospect, Ill.

[73] Assignee: UOP Inc., Des Plaines, Ill.

[*] Notice: The portion of the term of this patent subsequent to Dec. 11, 2001 has been disclaimed.

[21] Appl. No.: 773,953

[22] Filed: Sep. 9, 1985

Related U.S. Application Data

[63] Continuation-in-part of Ser. No. 693,337, Jan. 22, 1985, abandoned.

[51] Int. Cl.$^4$ .............................................. C07C 37/11
[52] U.S. Cl. .................................... 568/794; 568/784; 568/789; 568/790; 502/78
[58] Field of Search ............... 568/780, 789, 790, 794, 568/784; 518/713, 714, 715; 502/78

[56] References Cited

U.S. PATENT DOCUMENTS

| | | | |
|---|---|---|---|
| 2,973,384 | 2/1961 | Hayashi | 518/715 |
| 3,392,106 | 7/1968 | Mason et al. | 518/715 |
| 3,962,140 | 6/1976 | Alcorn et al. | 518/714 |
| 4,180,516 | 12/1979 | Chang | 518/713 |
| 4,472,535 | 9/1984 | Chang | 518/714 |
| 4,487,984 | 12/1984 | Imai | 585/454 |

FOREIGN PATENT DOCUMENTS

| | | | |
|---|---|---|---|
| 2538266 | 6/1984 | France | 502/78 |
| 833976 | 5/1960 | United Kingdom | 518/713 |
| 0803969 | 2/1981 | U.S.S.R. | 502/78 |

*Primary Examiner*—Werren B. Lone
*Attorney, Agent, or Firm*—Thomas K. McBride; John F. Spears, Jr.; Raymond H. Nelson

[57] ABSTRACT

Alkylaromatic compounds may be synthesized by reacting an aromatic compound with an alkylating agent comprising a mixture of gases, including carbon-monoxide and hydrogen at alkylation conditions in the presence of a dual-function-catalyst. The catalyst system which is employed for this reaction will comprise (1) a composite of oxides of copper and chromium and (2) an aluminosilicate which may be either in crystalline or amorphous form.

15 Claims, No Drawings

PROCESS FOR THE SYNTHESIS OF ALKYLAROMATIC COMPOUNDS

CROSS-REFERENCE TO RELATED APPLICATION

This application is a continuation-in-part of copending application Ser. No. 693,337 filed Jan. 22, 1985, now abandoned, all teachings of which are incorporated herein by reference thereto.

BACKGROUND OF THE INVENTION

Alkylaromatic compounds and particularly alkylaromatic hydrocarbons will find a wide variety of uses in the chemical field. For example, toluene, which may be obtained by the catalytic reforming of petroleum, by fractional distillation of coal tar light oil, by extraction from coal gas, etc., is used in aviation gasoline as well as high octane blending stock, as a solvent, in paints and coatings, rubber cement, in medicines, dyes, perfumes or as an intermediate in the preparation of polyurethane resins, explosives, detergents, etc. Likewise, the isomeric xylenes also find a wide variety of uses. For example, o-xylene may be used in vitamin and pharmaceutical syntheses, in dyes, insecticides, in the manufacture of phthalic anhydride; m-xylene may be used as a solvent, as an intermediate for dyes and organic syntheses; p-xylene is used in the synthesis of terephthalic acid which is an intermediate for the production of synthetic resins and fibers such as Dacron, Myler, etc., while mixtures of the isomeric xylenes may be used in aviation gasoline, protective coatings, as a solvent for alkyl resins, lacquers, enamels, rubber cements, etc. Other alkylaromatic hydrocarbons which are also useful in commercial chemical processes include cumene (isopropylbenzene) which is used as an additive to aviation gasoline or in the production of other chemicals such as phenol, acetone, etc., and ethylbenzene which is used as a solvent and diluent or as an intermediate in the production of styrene.

As hereinbefore set forth, the simple alkylaromatics such as toluene and the isomeric xylenes are obtained from petroleum or gas. However, these compounds may also be synthesized by treating an aromatic compound such as benzene or toluene with an alkylating agent comprising a synthesis gas which contains hydrogen and carbon monoxide and in some instances carbon dioxide. One such process is described in U.S. Pat. No. 4,487,984 in which the aromatic compound is reacted with a synthesis gas in the presence of a catalyst system which comprises a composite of oxides of copper, zinc and aluminum or chromium in conjunction with an aluminosilicate. However, as will hereinafter be shown in greater detail, we have now discovered that an aromatic compound may be alkylated utilizing, as the alkylating agent, a synthesis gas in which the catalyst which is employed to effect the alkylation reaction comprises a composite of oxides of only zinc and chromium along with an aluminosilicate. The utilization of the catalyst system of our invention as opposed to the catalyst system described in the aforementioned patent will permit the use of higher reaction temperatures inasmuch as our catalyst system will be more stable at higher temperatures due to the absence of the oxide of copper in the composite. This is due to the fact that the copper oxide which is present in the catalyst system of the prior patent will have a tendency to lose its activity at relatively high operating temperature, i.e. above about 280° C. and thus render the catalyst system relatively inoperable. The ability to use higher operating pressures may be of an advantage in the event that higher temperatures, shorter space times may become commercially attractive to the operator of the reaction system. In addition, by utilizing only the oxides of zinc and chromium as one component of the catalyst system, it is also possible to utilize, as the aluminosilicate component of the system, a compound which does not require a relatively high silica-to-alumina content, thereby permitting the employment of other aluminosilicates which may be relatively less expensive, thereby lowering the cost of operation of the desired reaction.

In addition to the aforementioned U.S. patent, there are also other patents which describe catalyst compositions similar in nature to the composition employed in this process. However, the catalyst set forth in these references is utilized for various reactions other than an alkylation reaction. For example, U.S. Pat. No. 3,392,106 describes a hydrocracking process in which a catalyst comprising a crystalline aluminosilicate composite with a zinc compound and a compound of a metal of Group IV of the Periodic Table is used to treat a petroleum feedstock at hydrocracking conditions to convert said petroleum feedstock into components which are useful to increase the octane number of fuels such as gasoline. U.S. Pat. No. 4,180,516 discloses a catalyst comprising as a first component a carbon monoxide reduction catalyst such as a zinc-chromium mixture composited with a crystalline aluminosilicate zeolite to convert snythesis gas to aromatic hydrocarbons. In like manner, U.S. Pat. No. 3,699,181 discloses a catalyst comprising a Group VIB metal of the Periodic Table such as chromium, molybdenum or tungsten composited on a synthetic mordenite base to effect an alkyl transfer of alkylaromatics. An example of this process is subjecting toluene to the action of the catalyst to prepare benzene, toluene and isomeric xylenes. In a similar vein, U.S. Pat. No. 3,915,895 also discloses a catalyst for the disproportionation of alkylaromatic compounds such as toluene utilizing as a catalyst for this process a composite comprising hydrogen, mordenite and a Group IB metal such as copper or silver impregnated on the mordenite and also containing, if so desired, a Group VIB metal. U.S. Pat. No. 4,472,535 is drawn to a method for converting synthesis gas selectively to ethane utilizing a catalyst comprising a crystalline zeolite component in conjunction with a metal such as chromium, zinc or aluminum along with, if so desired, potassium. In addition to these U.S. patents, French Patent No.2538-266-A discloses a catalyst comprising two transition metals in association with a dealuminized active mordenite to produce for use in the conversion of synthesis gas to organic compounds containing a high ethylene content.

As was hereinbefore set forth, none of the aforementioned patents disclose an alkylation process wherein alkylaromatic compounds may be prepared in a one-step process by treating an aromatic compound with synthesis gas in the presence of a catalyst system of the type hereinafter set forth in greater detail.

SUMMARY OF THE INVENTION

This invention relates to a process for the synthesis of alkylaromatic compounds and to a catalyst system comprising a dual-catalyst or dual-function-catalyst. More particularly, the invention is concerned with a process for the synthesis of alkylaromatic compounds by reacting an aromatic compound of the type hereinafter set forth in greater detail with a mixture of gases containing as predominant components thereof, carbon monoxide and hydrogen, the synthesis reaction being effected in the presence of a dual-catalyst or dual-function-catalyst system.

It is therefore an object of this invention to provide a process for the synthesis of an alkylaromatic compound.

In one aspect, an embodiment of this invention resides in a process for the synthesis of an alkylaromatic compound which comprises reacting an aromatic compound with a mixture of gases comprising hydrogen and carbon monoxide at reaction conditions in the presence of a catalyst system comprising (1) a composite of oxides of zinc and chromium, and (2) an aluminosilicate, and recovering the resultant alkylaromatic compound.

A specific embodiment of this invention is found in a process for the synthesis of an alkylaromatic compound which comprises reacting an aromatic compound such as benzene with a mixture of gases comprising hydrogen and carbon monoxide in which the molar ratio of hydrogen to carbon monoxide in said mixture is in a range of from about 1:1 to about 20:1 moles of hydrogen per mole of carbon monoxide at a temperature in the range of from about 200° C. to about 500° C. and a pressure in the range of from about 1 to about 400 atmospheres in the presence of a catalyst system comprising a composite of oxides of zinc and chromium and an aluminosilicate, and recovering the resultant alkylaromatic mixture comprising toluene, ethylbenzene, o-xylene, m-xylene, p-xylene and cumene.

Other objects and embodiments will be found in the following further detailed description of the invention.

DETAILED DESCRIPTION OF THE INVENTION

As hereinbefore set forth, the present invention is concerned with a process for the synthesis of alkylaromatic compounds utilizing, as a catalyst system for effecting the reaction, a combination of a composite of the oxides of zinc and chromium along with an aluminosilicate. The aromatic compound is alkylated by utilizing, as the alkylating agent thereof, a mixture of gases which include carbon monoxide and hydrogen. This alkylating agent which is used to produce the desired compound comprises a mixture of gases and preferably a mixture of carbon monoxide and hydrogen which may also include some carbon dioxide and is commercially known as synthesis gas. The hydrogen and carbon monoxide which are present in this mixture of gases may be in various, proportions, the preferred proportions for the present invention being that in which the mole ratio of hydrogen to carbon monoxide is in a range of from about 1:1 up to about 20:1 moles of hydrogen per mole of carbon monoxide. In addition to the carbon monoxide and hydrogen, carbon dioxide may be present in a range of from 0.01:1 to 1:1 moles of carbon dioxide per mole of carbon monoxide, as well as other gases which may be present in relatively small amounts, said gases including methane, water, oxygen and nitrogen. The synthesis gas which is used as the alkylating agent may be obtained from any source such as by the high temperature action of steam on carbon or natural gas, by the partial oxidation of natural gas, etc.

The aromatic compounds which may be alkylated with the aforesaid synthesis gas may include aromatic hydrocarbons such as benzene, toluene, ethylbenzene, cumene, naphthalene, chrysene, anthracene, phenanthrene or an aromatic compound which possesses a substituent such as phenol, cresol, etc.

The synthesis of the alkylaromatic compound which is effected by reacting an aromatic compound with a synthesis gas will employ reaction conditions which include elevated temperatures and pressures. Reaction temperatures which will be employed will be in a range of from about 200° up to about 500° C. or more. Likewise, elevated pressures will range from about 1 to about 400 atmospheres. As was previously stated, the ability to employ relatively high operating pressures is possible due to the use of the particular catalyst system which will hereinafter be set forth in greater detail. While in one embodiment of the invention the pressures which are utilized to effect the alkylation reaction will comprise the autogenous pressure of the synthesis gas, it is also contemplated within the scope of this invention that the synthesis gas may afford only a partial pressure, especially when relatively high operating pressures are employed, the remaining portion of the operating pressure being supplied by the introduction of a substantially inert gas such as nitrogen, helium, argon, etc. into the reaction zone.

The catalyst system which is employed in the synthesis of the alkylaromatic compound according to the process of this invention comprises a composite of oxides of zinc and chromium as one component, and as a second component, an aluminosilicate which may be selected from many forms including those hereinafter set forth in greater detail. The resulting catalyst system will possess many desirable characteristics which will enable its use viable in obtaining the desired alkylaromatic compound. The catalyst system may comprise either a dual-catalyst or a dual-function-catalyst. As was previously mentioned, one component comprises a composite of oxides of zinc and chromium. This composite may be prepared by coprecipitating soluble salts of zinc and chromium. This composite may be prepared by coprecipitating soluble salts of zinc and chromium followed by a neutralization step to precipitate the desired salts. Examples of soluble salts of metals which may be employed will include zinc chloride, zinc nitrate, zinc dichromate, zinc sulfate, chromic acid, chromic acetate, chromic sulfate, etc. It is to be understood that the aforementioned soluble salts are only representative of the type of salts which may be employed to prepare the desired composite, and that the present invention is not necessarily limited thereto.

The aforesaid salts are admixed in a suitable solvent such as water and after dissolving the salts which are present in an amount so that the finished catalyst system will contain a predetermined amount of metals in the form of oxides, the solution is neutralized by the addition of a neutralizing agent such as sodium hydroxide, potassium hydroxide, lithium hydroxide, ammonoium hydroxide, sodium carbonate, potassium carbonate, lithium carbonate, ammonium carbonate, etc. to a pH of about 7, the neutralization of the solution acting to promote the precipitation of the compounds. After formation of the precipitate has occurred, it is then allowed to age for a predetermined period of time which may range from about 0.1 to about 1 hour or more at an elevated temperature of from about 50° to about 75° C. or higher. Upon completion of the aging period, the precipitate is then rinsed with deionized water to remove the alkaline material and dried, preferably at a temperature slightly in excess of 100° C., i.e., 110° C. The precipitate may then be sized to a desired mesh which may range from about 20 to about 60 mesh or, if so desired, the precipitate may then be calcined at an elevated temperature in the range of from about 250° C. to about 500° C. or higher in nitrogen or air for a period of time which may range from about 2 to about 4 hours.

The second component of the dual-catalyst system will comprise an aluminosilicate which may be in either crystalline or amorphous form. It is contemplated within the scope of this invention that various types of alumlinosilicates may be employed, including for example, zeolites such as X zeolite, Y zeolite, L zeolite, zeolite, mordenite, etc. Other aluminosilicates may comprises those which are known as the pentasil crystalline aluminosilicates which possess a silicon (SiO$_2$) to aluminum (Al$_2$O$_3$) ratio greater than about 5:1. The zeolitic crystalline aluminosilicates may occur both naturally or may be synthesized. In hydrated form the crystalline aluminosilicates generally encompass those zeolites represented by Formula 1 below:

$$M_{2/n}O:Al_2O_3:wSiO_2:yH_2O \qquad \text{Formula 1}$$

where "M" is a cation which balances the electrovalence of the aluminum-centered tetrahedra and which is generally referred to as an exchangeable cationic site, "n" represents the valence of the cation, "w" represents the moles of SiO$_2$, and "y" represents the moles of water. The generalized cation "M" may be monovalent, divalent or trivalent or mixtures thereof.

Types of well-known crystalline aluminosilicates include zeolites in either the X or Y form. The X zeolite in the hydrated or partially hydrated form can be represented in terms of mole oxides as shown in Formula 2 below:

$$(0.9-0.2)M_{2/n}O:Al_2O_3:(2.50-0.5)SiO_2:yH_2O \qquad \text{Formula 2}$$

where "M" represents at least one cation having a valence of not more than 4, "n" represents the valence of "M" and "y" the degree of hydration of the crystal. As noted from Formula 2, the SiO$_2$/Al$_2$O$_3$ mole ratio of X zeolite is 2.5—0 5. The cation "M" may be one or more of a number of cations such as a hydrogen cation, an alkali metal cation, or an alkaline earth cation, or other selected cations, and is generally referred to as an exchangeable cationic site. As the X zeolite is initially prepared, the cation "M" is usually predominately sodium, that is, the major cation at the exchangeable cationic sites is sodium, and the zeolite is therefore referred to as a sodium-X zeolite. Depending upon the purity of the reactants used to make the other cations mentioned above may be present, however, as impurities. The Y zeolite in the hydrated or partially hydrated form can be similarly represented in terms of mole oxides as in Formula 3 below:

$$(0.9-0.2)M_{2/n}O:Al_2O_3:wSiO_2:yH_2O \qquad \text{Formula 3}$$

where "M" is at least one cation having a valence not more than 4, "n" represents the valence of "M", "w" is a value greater than about 3 up to about 6, and "y" is a value up to about 9 depending upon the identity of "M" and the degree of hydration of the crystal. The SiO$_2$/Al$_2$O$_3$ mole ratio of Y zeolites can thus be from about 3 to about 6. Like the X zeolite, the cation "M" may be one or more of a variety of cations but, as the Y zeolite is initially prepared, the cation "M" is also usually predominately sodium. A Y zeolite containing predominately sodium cations at the exchangeable cationic sites is therefore referred to as a sodium-Y zeolite.

Another type of aluminosilicate which may be used comoprises the pentasil family of zeolites which can also be identified in terms of mole ratios of oxides as follows:

$$0.9-0.2M_{2/n}O:Al_2O_3:ySiO_2:zH_2O$$

wherein M is a cation, n is the valence of that cation, y is at least 5, and z is from 0 to 40. In a preferred synthesized form, the zeolite has a formula, in terms of mole ratios of oxides, as follows:

$$0.9-0.2M_{2/n}O:Al_2O_3:5-100\ SiO_2:zH_2O$$

and M is selected from the group consisting of a mixture of alkali metal cations, especially sodium, and tetraalkylammonium cations, the alkyl groups of which preferably contain 2–5 carbon atoms.

Members of the pentasil family of zeolites possess a definite distinguishing crystalline structure whose X-ray diffraction pattern shows the following significant lines:

TABLE 1

| Interplanar Spacing d(A) | Relative Intensity |
|---|---|
| 11.2 ± 0.2 | 60–100 |
| 10.1 ± 0.2 | 60–100 |
| 6.73 ± 0.14 | 0–20 |
| 4.63 ± 0.08 | 0–20 |
| 3.86 ± 0.07 | 40–60 |
| 3.72 ± 0.07 | 20–60 |
| 2.01 ± 0.02 | 0–2 |

These values as well as all other X-ray data are determined by standard techniques.

In Table 1 the relative intensities are given as relative values. It should be understood that this X-ray diffraction pattern is characteristic of all the species of pentasil family zeolite compositions. Ion-exchange of the sodium ion with cations reveals substantially the same pattern with some minor shifts in interplanar spacing and variation in relative intensity. Other minor variations can occur depending on the silicon-to-aluminum ratio of the particular sample as well as if it had been subjected to thermal treatment. Ammonium is a preferred cátion for ion-exchange.

The two components of the catalyst system, namely the oxide of zinc and chromium being one components, while the other component comprises an aluminosilicate, may be used as a dual-function-catalyst, that is, the two catalysts may be loaded separately in the reactor in a multiplicity of separate layers or in an admixture of the two components in a mixed layer. Alternatively, the dual-function-catalyst may be prepared so that a homogeneous mixture of the two components is obtained. Various methods may be utilized to attain this type of catalyst mixture, for example, the aluminosilicate can be bound in a mixture of coprecipitated zinc and chromium hydroxides followed by a calcination of the resulting mixture in an oxygen atmosphere such as that oC provided by air at a temperature in excess of about 200 for a period of about 1 to 10 hours followed by reduction in a hydrogen or nitrogen-hydrogen atmosphere to afford the active catalyst. Other procedures for obtaining the desired catalyst mixture may be a physical admixture of the aluminosilicate with mixtures of zinc chromate, zinc acetate, chromium acetate, zinc oxide, chromium oxide, etc. followed by a thermal treatment similar in nature to that hereinbefore set forth, and reduction; impregnating a zinc oxide-bound aluminosilicate which may contain from about 10% to about 90% by weight of zinc oxide, with an aqueous solution of chromic acid followed by calcination and reduction, or by impregnating an aluminum .ohosphate-bound aluminosilicate with aqueous or alcoholic solutions of compounds containing zinc and chromium of the type hereinbefore set forth, again followed by calcination at a temperature of above about 200oC and reduction with hydrogen to form the active catalyst. In the preferred embodiment of this invention, the oxide of zinc is present in the composite in a range of from about 10% to about 99% by weight while the oxide of chromium is present in an amount in the range of from about 1% to about 90% by weight of the composite.

The process which involves the synthesis of alkylaromatics from aromatic compounds, carbon monoxide and hydrogen may be effected in any suitable manner and may comprise either a batch or continuous type operation. For example, when a batch type operation is employed, the aromatic compound which is to undergo alkylation is placed in an appropriate pressure-resistant apparatus such as an autoclave of the rotating, mixing or stirring type along with the dual-function catalyst. The autoclave is sealed and a mixture of hydrogen and carbon monoxide along with carbon dioxide, if so desired, is charged to the autoclave until the desired operating pressure within the range hereinbefore specified is attained. Following this, the autoclave is heated to the desired operating temperature and the alkylation reaction is allowed to proceed for a predetermined period of time which may range from about 0.5 up to about 10 hours or more in duration. Upon completion of the reaction period, heating is discontinued and after the autoclave has returned to room temperature, any excess pressure which is still present is discharged and the autoclave is opened. The reaction mixture is recovered from the autoclave, separated from the catalyst by conventional means such as filtration, decantation, centrifugation, etc. and subjected to fractional distillation, usually under reduced pressure, whereby the various alkylaromatics which have been formed during the reaction are separated and recovered.

Alternatively, the alkylation of the aromatic compound with the gaseous mixture may be effected in a continuous manner of operation. When such a type of operation is performed, the aromatic coapound which is to undergo alkylation and the gaseous mixture of hydrogen and carbon monoxide which forms the alkylating agent are continuously charged to a reactor containing the catalyst system and which is maintained at the proper operating conditions of temperature and pressure. After passage of the reaction components through the reactor for a predetermined period of time, the reactant effluent is continuously withdrawn therefrom and subjected to conventional means of separation whereby the alkylaromatic components comprising the reaction products are separated from any unreacted aromatic compounds, and recovered, the latter being recycled back to the reactor to form a portion of the feedstock.

Due to the nature of the catalyst sytem, various modes of continuous operation may be employed to effect the alkylation reaction. For example, the catalyst sytem may be Positioned in the reactor as a fixed bed, either in multilayers of such components of the catalyst system or as a single fixed bed of the dual-function catalyst which comprises both components of the system as a single entity. The aromatic compound which is to undergo alkylation and the alkylating agent are continuously passed through the bed of catalyst in either an upward or downward flow and the reactor effluent is continuously recovered. Another method of effecting the continuous alkylation operation comprises the moving bed type in which the catalyst system either in multilayers or as a single dual-function catalyst and the reaction components are passed through the reactor either concurrently or countercurrently to each other. A third type of continuous type of operation which may be employed comprises the slurry type of operation in which the catalyst system in the form of a dual-catalyst or a dual-function catalyst may be admitted to the reactor as a slurry in the aromatic compound which is to undergo alkylation. It is to be understood that regardless of the type of continuous operation which is employed, the separation of the reaction product from any unreacted aromatic compound is effected in a manner previously described, the desired product being recovered while the aforesaid unreacted aromatic compound is recycled back to the reactor.

Examples of alkylaromatic compounds which may be obtained by the alkylation of the present invention will include, but not be limited to, toluene, ethylbenzene, o-xylene, m-xylene, p-xylene, n-propylbenzene, isopropylbenzene (cumene), sec-butylbenzene, o-ethyltoluene, m-ethyltoluene, p-ethyltoluene, 1,3,5-trimethylbenzene, 1,2,4-trimethylbenzene, etc.

The following examples are given for purposes of illustrating the alkylation process and the dual-function-catalyst system of the present invention. However, it is to be understood that these examples are given merely for purposes of illustration and that the present process is not necessarily limited thereto.

EXAMPLE 1

A catalyst system which was used in the synthesis of alkylaromatics was prepared by dissolving 138 grams of chromium nitrate nonahydrate and 291 grams of zinc nitrate hexahydrate in 1.5 liters of deionized water. The mixture was stirred and heated to a temperature of about 65oC. In addition, 150 grams of sodium carbonate was dissolved in 1.6 liters of deionized water which was also heated to a temperature of 65oC. The two solutions were then admixed by addition of the solutions to a vessel containing hot deionized water. A precipitate formed following which further neutralization was accomplished by adding an additional amount of sodium carbonate and the precipitate was aged for a period of 20 minutes accompanied by continuous stirring. After aging, the precipitate was filtered, washed with water and dried at a temperature of 110oC for a period of 12 hours. The precipitate was then sized to 16–40 mesh and calcined in a nitrogen atmosphere at a temperature of 150oC for a period of one hour and at 300 for a period of four hours. The final composite contained 5.0% of zinc, 16.5% chromium, and had an ABD of 0.476.

The second component of the dual-function-catalyst was prepared by admixing an MFI zeolite (a pentasil crystalline aluminosilicate) in powder form which had been previously washed with dilute $HNO_3$ *with a* 33 wt. % solution of aluminum phosphate. The solution was oil dropped. After recovery of the particles from the oil dropping, the °C in flowing particles were calcined at a temperature of 350 nitrogen containing 2% oxygen for a period of two hours following which the temperature of the calcination was raised to 550°C and maintained thereat for a period of 18 hours under the same atmosphere. At the end of the 18 hour period, the calcining atmosphere was changed to air for a period of two hours and thereafter the calcining material was steamed at a temperature of 600°C for a period of two hours. After allowing the zeolite to return to room temperature, the particles were sized to a 16-40 mesh.

The two components of the catalyst system were then mixed in a 1:1 ratio by volume and 10 cc of the catalyst was loaded into a reactor. The catalyst was reduced by passing hydrogen over the catalyst at a temperature of 350°C for a period of 16 hours.

The alkylation of an aromatic compound was accomplished by passing a mixture of benzene and synthesis gas over the catalyst for a period of 3-4 hours while °C and a pressure maintaining a reaction temperature of 360 of 1800 psig. The molar ratio of the benzene and synthesis gas was 10.2:1:0.24:2.6 moles of benzene per mole of carbon monoxide per mole of carbon dioxide per mole of hydrogen, the addition of the reactants being effected at a liquid hourly space velocity (LHSV) of 12 hours$^{-1}$ based on the benzene.

Analysis of the product showed that there had been a 1% conversion of the benzene and a 22% conversion of the carbon monoxide and carbon dioxide. In addition, the analysis also showed that there had been a 98% selectivity to toluene with a 2% selectivity to paraffins containing from 1 to 4 carbon atoms. The analysis did not disclose the formation of any elthylbenzene, isomeric xylenes or propylbenzenes.

EXAMPLE II

A repeat of the above experiment was performed using similar conditions with the exception of an increased reaction temperature of 435°C and a feedstream of benzene and synthesis gas in which the mole ratio of benzene to carbon monoxide and carbon dioxide/ was 7:1, the mole ratio of hydrogen to carbon monoxide was 8.1:1 resulting in a 9% conversion of benzene and a 68% conversion of carbon monoxide and carbon dioxide.

Analysis also showed that there had been a 75 mole percent selectivity to toluene; 5 mole percent selectivity to ethylbenzene; 6 mole percent selectivity to isomeric xylenes; 8 mole percent selectivity to propylbenzene and 5 mole percent selectivity to hydrocarbons containing from 1 to 4 carbon atoms.

EXAMPLE III

An experiment was performed in which the zinc and chromium composite and an MFI zeolite components were mixed in a 3.4:1 ratio by volume and 10 cc of the catalyst was loaded into a reactor. The catalyst was reduced in a manner similar to that set forth above. A mixture of benzene and synthesis gas was passed over the catalyst for a period of about four hours using similar conditions to those described above in Example II.

Analysis of the product showed that there had beren an 8% conversion of benzene and a 64% conversion of carbon monoxide and carbon dioxide. In addition, the analysis also showed that there had been 87 mole percent selectivity to toluene; 3 mole percent selectivity to ethylbenzene; 6 mole percent selectivity to isomeric xylenes; 3 mole percent selectivity to propylbenzenes and less than 1 mole percent selectivity to hydrocarbons containing from 1 to 4 carbon atoms.

EXAMPLE IV

A catalyst was prepared in a manner similar to that set forth in Example 1 and 10 grams of the finished catalyst system comprising a mixture of oxides of zinc and chromium and an MFI zeolite was placed in a reactor. A mixture of benzene and synthesis gas was passed over the catalyst for a period of about four hours while maintaining a reaction temperature of 350°C and a pressure of 1800 psig. The molar ratio of the various components of the feed were a benzene/carbon monoxide and carbon dioxide molar ratio of 1; a carbon dioxide/carbon monoxide mole ratio of 0.24:1; and an $H_2$/C mole ratio of 2.6:1. The addition of the benzene and synthesis gas was effected at a LHSV of 12 hours$^{-1}$ based on the benzene.

The product was analyzed and it was found that there had been a 5% conversion of the benzene and a 13% conversion of the carbon monoxide and carbon dioxide. In addition, there was also shown a 92% selectivity to toluene; a 2% selectivity to ethylbenzene; a 5% selectivity to isomeric xylenes; a 2% selectivity to propylbenzene and a 1% selectivity to paraffins containing from 1 to 4 carbon atoms.

EXAMPLE V

A dual-functional catalyst consisting of a homogeneous mixture of the two components was prepared by coprecipitating a mixture of zinc and chromium nitrates with sodium carbonate using a similar procedure to that described in Example I with the exception that after washing with water the precipitate was slurried in two liters of water. An MFI zeolite in powder form which had previously been calcined in a muffle oven at a temperature of 350°C for a period of one hour and at a temperature of 550 period of two hours was added to the slurry and mixed. The solid was recovered by filtration and dried at a temperature of 110°C for a period of 12 hours. The particles were then sized to 16-40 mesh and calcined in a nitrogen atmosphere at a temperature of 300°C for a period of four hours. The final composite contained 53.1% zinc, 13.8% chromium, 1.3% aluminum and 13.1% silica on a weight basis.

The catalyst was used for the synthesis of alkylaromatics employing a similar procedure to that described in Example II, said reaction resulting in a 4.7% conversion of benzene and a 67% conversion of carbon monoxide and carbon dioxide.

Analysis of the product showed that there had been 90% selectivity to toluene; 3% solectivity to ethylbenzene; 5% selectivity to isomeric xylenes and 1% selectivity to paraffins containing 1 to 4 carbon atoms.

EXAMPLE VI

In this example, various catalyst systems were prepared utilizing different aluminosilicates. The catalyst preparation was similar to that set forth in Example I above, the final catalyst which was used for the synthesis of alkylaromatics comprising 10 grams of the system in which the two components were in a 1:1 volume ratio. The aluminosilicate in catalyst A comprised a mordenite containing 55% of alumina; catalyst B comprised a dealuminated mordenite containing 50% alumina; catalyst C comprised a hydrogen-form Y zeolite containing 50% silica; catalyst D comprised a hydrogen-form dealuminated Y zeolite containing 50% silica and catalyst E comprised a hydrogen-form L zeolite containing 50% silica.

The catalysts were placed in separate reactors and a feed stream of benzene and synthesis gas was passed over the catalyst at a LHSV of 11.5 hours$^{-1}$ based on the benzene at a pressure of 1800 psig while maintaining the inlet temperature of the reactor at 400o C The mole ratio of reactants comprised 7:1:8.6 moles of benzene per mole of C0 plus $CO_2$ per mole of hydrogen. The synthesis gas was passed over the catalyst for a period of four hours. The results of the tests are set forth in Tables 2 and 3 below:

TABLE 2

| Catalyst | Benzene Conversion % | CO & $CO_2$ Conversion % | % CO & $CO_2$ to Aromatics |
|---|---|---|---|
| A | 4.6 | 49.5 | 37.7 |
| B | 4.1 | 60.8 | 45.7 |
| C | 5.9 | 58.7 | 55.7 |
| D | 5.7 | 53.8 | 50.7 |
| E | 3.0 | 32.3 | 25.5 |

TABLE 3

| | SELECTIVITY (MOLE PERCENT) | | | | | |
|---|---|---|---|---|---|---|
| Catalyst | Toluene | Xylenes | Trimethylbenzenes | Ethylbenzene | Propyl benzene | $C_1$-$C_4$ |
| A | 76 | 3 | 0 | 8 | 7 | 5 |
| B | 69 | 3 | 2 | 8 | 13 | 6 |
| C | 83 | 6 | 1 | 6 | 5 | 1 |
| D | 84 | 6 | 1 | 5 | 4 | 1 |
| E | 90 | 1 | 0 | 1 | 4 | 4 |

It is apparent from the above Tables that various types of aluminosilicates may be employed as one component of a catalyst system along with a composite of oxides of zinc and copper to effect the synthesis of alkylaromatic compounds by treating an aromatic compound with an alkylating agent comprising a mixture of gases as exemplified by synthesis gas.

We claim as our invention:

1. A process for the synthesis of an alkyaromatic compound which comprises reacting an aromatic compound with a mixture of gases comprising hydrogen and carbon monoxide at reaction conditions in the presence of a catalyst system consisting essentially of (1) a composite consisting of oxides of zinc and chromium, and (2) an aluminosilicate, and recovering the resultant alkylaromatic compound.

2. The process as set forth in Claim 1 in which said reaction conditions include a temperature in the range of from about 200o to about 500oC and a pressure in the range of from about 1 to about 400 atmospheres.

3. The process as set.forth in Claim 1 in which the mole ratio of hydrogen to carbon monoxide in said mixture of gases is in a range of from about 1:1 to about 20:1 moles of hydrogen per mole of carbon monoxide.

4. The process as set forth in Claim 1 in which said mixture of gases contains carbon dioxide in a mole ratio in a range of from about 0.01:1 to about 1:1 moles of carbon dioxide per mole of carbon monoxide.

5. The process as set forth in Claim 1 in which the ratio of silicon to aluminum in said aluminosilicate is greater than about 2:1.

6. The process as set forth in Claim 1 in which said oxide of zinc is present in said composite of oxides in an amount in the range of from about 10% to about 99% by weight of said composite.

7. The process as set forth in Claim 1 in which said oxide of chromium is present in said composite of oxides in an amount in the range of from about 1% to about 90% by weight of said composite.

8. The process as set forth in Claim 1 in which said aluminosilicate comprises a Y zeolite.

9. The process as set forth in Claim 1 in which said aluminosilicate comprises an X zeolite.

10. The process as set forth in Claim 1 in which said aluminosilicate comprises an L zeolite.

11. The process as set forth in Claim 1 in which said aluminosilicate comprises a mordenite.

12. The process as set forth in Claim 1 in which said aluminosilicate comprises a pentasil crystalline aluminosilicate.

13. The process as set forth in Claim 1 in which said aromatic compound comprises benzene and said alkylaromatic compound is a mixture comprising toluene, ethylbenzene, o xylene, m-xylene, p-xylene and cumene.

14. The process as set forth in Claim 1 in which said aromatic compound comprises toluene and said alkylaromatic compound is a mixture comprising o-xylene, m-xylene, p-xylene, o-ethyltoluene, m-ethyltoluene, p-ethyltoluene, o-isopropyltoluene, m-isopropyltoluene and p-isopropyltoluene.

15. The process as set forth in Claim 1 in which said aromatic compound comprises phenol and said alkylaromatic compound is a mixture comprising o-cresol, m-cresol, p-cresol, o-ethylphenol, m-ethylphenol, p-ethylphenol, o-isopropylphenol, m-isopropylphenol and p-isopropylphenol.

* * * * *